United States Patent [19]
Dorsch et al.

[11] Patent Number: 5,883,090
[45] Date of Patent: Mar. 16, 1999

[54] ENDOTHELIN RECEPTOR ANTAGONISTS

[75] Inventors: Dieter Dorsch, Ober-Ramstadt; Mathias Osswald, Zwingenberg; Werner Mederski, Erzhausen; Claudia Wilm, Mühltal; Claus Jochen Schmitges, Darmstadt; Maria Christadler, Rödermark, all of Germany

[73] Assignee: Merck Patent Gesellschaft mit Beschrankter Haftung, Germany

[21] Appl. No.: 849,344

[22] PCT Filed: Sep. 19, 1996

[86] PCT No.: PCT/EP96/04111

§ 371 Date: Jun. 6, 1997

§ 102(e) Date: Jun. 6, 1997

[87] PCT Pub. No.: WO97/13758

PCT Pub. Date: Apr. 17, 1997

[30] Foreign Application Priority Data

Oct. 9, 1995 [DE] Germany .................. 195 37 548.3

[51] Int. Cl.[6] .................. A61K 31/54; A01N 43/58; C07D 285/16; C07D 237/00
[52] U.S. Cl. .................. 514/222.5; 514/252; 514/253; 544/8; 544/239
[58] Field of Search .................. 514/252, 253, 514/222.5; 544/239, 8

[56] References Cited

U.S. PATENT DOCUMENTS 2,832,780  4/1958  King et al. .................. 260/250

FOREIGN PATENT DOCUMENTS 046069  2/1982  European Pat. Off. .

*Primary Examiner*—Richard L. Raymond
*Assistant Examiner*—Tamthom T. Ngo
*Attorney, Agent, or Firm*—Miller, White, Zelano, & Branigan P.C.

[57] ABSTRACT

This invention relates to pyridizinone derivatives of formula I

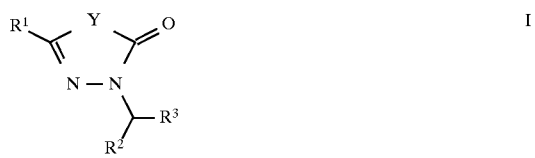

wherein the various substituents are defined in the specification, and salts thereof, which have useful pharmacological properties, in particular endothelin receptor-antagonistic properties. The compounds are thus useful for the treatment of illnesses associated with endothelin activities, such as hypertension, cardiac insufficiency, coronary heart disease, renal, cerebral and myocardial ischaemia, renal insufficiency, cerebral infarct, subarachnoid haemorrhage, arteriosclerosis pulmonary high blood pressure, inflammations, asthma, prostate hyperplasia, endotoxic shock and in complications after the administration of immunosuppressants which produce renal vasoconstriction.

5 Claims, No Drawings

ENDOTHELIN RECEPTOR ANTAGONISTS

This is a 371 application of PCT/EP96/04111, filed on Sep. 19, 1996.

The invention relates to compounds of the formula I

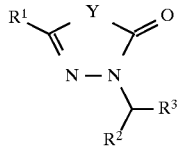

in which

Y is —C(R$^4$R$^{4'}$)C(R$^4$R$^{4'}$), —CR$^4$=CR$^{4'}$— or C(R$^4$R$^4$)S—,

R$^1$ is Het, Ar, R$^3$ or R$^4$,

R$^2$ is Ar or a

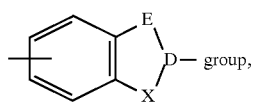 group, which is unsubstituted or mono- or disubstituted in the phenyl moiety by A, R$^3$, OR$^4$, NH$_2$, NHA, NA$_2$, NO$_2$, CN, Hal, NHCOR$^4$, NHSO$_2$R$^4$, COOR$^4$, COR$^4$, CONHSO$_2$R$^6$, O(CH$_2$)$_n$R$^3$, OPh, O(CH$_2$)$_n$OR$^4$ or S(O)$_m$R$^4$ or a

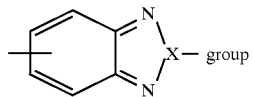 group which is unsubstituted or mono- or disubstituted in the cyclohexyldienyl moiety by A, R$^3$, OR$^4$, NH$_2$, NHA, NA$_2$, NO$_2$, CN, Hal, NHCOR$^4$, NHSO$_2$R$^4$, COOR$^4$, COR$^4$, CONHSO$_2$R$^6$, O(CH$_2$)$_n$R$^3$, OPh, O(CH$_2$)$_n$OR$^4$ or S(O)$_m$R$^4$, R$^3$ is CN, COOH, COOA, CONHSO$_2$R$^5$ or 1H-tetrazol-5-yl, R$^4$,R$^{4'}$ in each case independently of one another are H, A or phenyl or benzyl which is unsubstituted or monosubstituted by alkoxy, R$^5$ is A or Ar, R$^6$ is phenyl or naphthyl which is unsubstituted or mono-, di- or trisubstituted by A, OR$^5$, NH$_2$, NHA, NA$_2$, NO$_2$, CN or Hal, A is alkyl having 1–6 C atoms, in which one or two CH$_2$ groups can be replaced by O or S atoms or by —CR$^4$=CR$^4$— groups and also 1–7 H atoms can be replaced by F, or is benzyl, Ar is phenyl or naphthyl, which is unsubstituted or mono-, di- or trisubstituted by A, OR$^4$, NH$_2$, NHA, NA$_2$, NO$_2$, CN, Hal, NHCOR$^4$, NHSO$_2$R$^4$, COOR$^4$, COR$^4$, CONHSO$_2$R$^6$, O(CH$_2$)$_n$R$^3$, OPh, O(CH$_2$)$_n$OR$^4$ or S(O)$_m$R$^4$, Het is a mono- or binuclear saturated, unsaturated or aromatic heterocycle having 1 to 4 N, O and/or S atoms, bonded via N or C, which can be unsubstituted or mono-, di- or trisubstituted by Hal, A, R$^3$, NH$_2$, NHA, NA$_2$, CN, NO$_2$ and/or carbonyl oxygen, D is carbonyl or [C(R$^4$R$^{4'}$)]$_n$, E is CH$_2$, S or O, Hal is F, Cl, Br or I, X is O or S, m is 0, 1 or 2, n is 1 or 2, and their salts.

Similar compounds having indan and indene parent structures are disclosed in WO 93/08799, those with indole systems are disclosed in WO 94/14434, pyrimidine derivatives are disclosed in EP 0 526 708 A1 and phenyl and naphthyl compounds are disclosed in EP 0 617 001 A.

The invention was based on the object of finding novel compounds having useful properties, in particular those which can be used for the production of medicaments.

It has been found that the compounds of the formula I and their salts have very useful pharmacological properties combined with good tolerability. In particular, they exhibit endothelin receptorantagonistic properties and can therefore be employed for the treatment of illnesses such as hypertension, cardiac insufficiency, coronary heart disease, renal, cerebral and myocardial ischaemia, renal insufficiency, cerebral infarct, subarachnoid haemorrhage, arteriosclerosis, pulmonary high blood pressure, inflammations, asthma, prostate hyperplasia, endotoxic shock and in complications after the administration of immunosuppressants, such as, for example, cyclosporin, which can produce renal vasoconstriction, as well as other illnesses associated with endothelin activities.

The compounds exhibit, inter alia, a high affinity for the endothelin subreceptors ET$_A$ and ET$_B$. These actions can be determined by customary in vitro or in vivo methods, such as, for example, described by P. D. Stein et al., J. Med. Chem. 37, 1994, 329–331 and E. Ohlstein et al., Proc. Natl. Acad. Sci. USA 91, 1994, 8052–8056.

A suitable method for the determination of the hypertensive action is, for example, described by M. K. Brazil et al., J. Cardiovasc. Pharmacol. 22, 1993, 897–905 and J. Lange et al., Lab Animal 20, 1991, Appl. Note 1016.

The compounds of the formula I can be employed as pharmaceutical active compounds in human and in veterinary medicine, in particular for the prophylaxis and/or therapy of cardiac, circulatory and vascular diseases, especially of hypertension and cardiac insufficiency.

The invention relates to the compounds of the formula I and their salts, and to a process for the preparation of these compounds and their salts, characterized in that a compound of the formula II

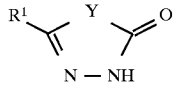

in which

R$^1$ and Y have the meaning indicated in Claim 1, is reacted with a compound of the formula III

in which

Q is Cl, Br, I or a free or reactive functionally modified OH group and

R$^2$ and R$^3$ have the meaning indicated in Claim 1, and/or in that in a compound of the formula I one or more radicals R$^1$, R$^2$ and/or R$^3$ are converted into one or more radicals R$^1$, R$^2$ and/or R$^3$, by, for example, i) hydrolysing an ester group to a carboxyl group,
ii) converting a carboxyl group into a sulfonamidocarbonyl group and/or converting a base or acid of the formula I into one of its salts.

In the above formulae, A has 1 to 6, preferably 1, 2, 3 or 4 carbon atoms. A is preferably methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore trifluoromethyl or pentafluoroethyl. Furthermore, A is cycloalkyl, preferably cyclopropyl.

E is preferably O, furthermore also $CH_2$ or S.

D is preferably $CH_2$, likewise carbonyl is also preferred.

n is preferably 1, furthermore preferably 2.

Hal is preferably F, Cl or Br, but also I.

Alkoxy is preferably methoxy, furthermore ethoxy, propyloxy, butyloxy or pentyloxy.

Ar is unsubstituted, preferably—as indicated—monosubstituted phenyl, specifically preferably phenyl, o-, m- or p-tolyl, o-, m- or p-ethylphenyl, o-, m- or p-propylphenyl, o-, m- or p-isopropylphenyl, o-, m- or p-tert-butylphenyl, o- m- or p-trifluoromethylphenyl, o-, m- or p-hydroxyphenyl, o-, m- or p-nitrophenyl, o-, m- or p-aminophenyl, o-, m- or p-(N-methylamino)-phenyl, o-, m- or p-acetamidophenyl, o-, m- or p-(trifluoromethoxy) phenyl, o-, m- or p-cyanophenyl, o-, m- or p-methoxyphenyl, o-, m- or p-ethoxyphenyl, o-, m- or p-carboxyphenyl, o-, m- or p-methoxy-carbonylphenyl, o-, m- or p-ethoxycarbonylphenyl, o-, m- or p-benzyloxycarbonylphenyl, o-, m- or p-(carboxymethoxy) phenyl, o-, m- or p-(methoxy-carbonyl-methyoxy) phenyl, o-, m- or p-(methoxycarbonyl-ethoxy) phenyl, o-, m- or p-(N,N-dimethylamino)phenyl, o-, m- or p-(N-ethylamino) phenyl, o-, m- or p-(N,N-diethylamino)phenyl, o-, m- or p-fluorophenyl, o-, m- or p-bromophenyl, o-, m- or p-chlorophenyl, o-, m- or p-(difluoromethoxy)phenyl, o-, m- or p-(fluoromethoxy)phenyl, o-, m- or p-formylphenyl, o-, m- or p-acetylphenyl, o-, m- or p-propionylphenyl, o-, m- or p-butyrylphenyl, o-, m- or p-pentanoylphenyl, o-, m- or p-(phenylsulfonamidocarbonyl)phenyl, o-, m- or p-phenoxyphenyl, o-, m- or p-methylthiophenyl, o-, m- or p-methylsulfinylphenyl, o-, m- or p-methylsulfinylphenyl, o-, m- or p-benzyloxyphenyl, o-, m- or p-cyanomethoxyphenyl, 2,3-, 2,4-, 2,5-, 2,6-, 3,4- or 3,5-(difluoromethoxy) (carboxymethoxy)phenyl, 2,3-, 2,4-, 2,5-, 2,6-, 3,4- or 3,5-methoxy-(carboxymethoxy)phenyl, 2,3-, 2,4-, 2,5-, 2,6-, 3,4- or 3,5-hydroxy(carboxymethoxy) phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-chloro-3-methyl-, 2-chloro-4-methyl-, 2-chloro-5-methyl-, 2-chloro-6-methyl-,2-methyl-3-chloro-, 2-methyl-4-chloro-, 2-methyl-5-chloro-, 2-methyl-6-chloro, 3-chloro-4-methyl, 3-chloro-5-methyl- or 3-methyl-4-chlorophenyl, 2-bromo-3-methyl, 2-bromo-4-methyl, 2-bromo-5-methyl-, 2-bromo-6-methyl, 2-methyl-3-bromo-, 2-methyl-4-bromo-, 2-methyl-5-bromo-, 2-methyl-6-bromo-, 3-bromo-4-methyl, 3-bromo-5-methyl- or 3-methyl-4-bromophenyl, 2,4- or 2,5-dinitrophenyl, 2,5- or 3,4-dimethoxyphenyl, 3-nitro-4-chlorophenyl, 2-amino-3-chloro-, 2-amino-4-chloro, 2-amino-5-chloro- or 2-amino-6-chlorophenyl, 2-nitro-4-N,N-dimethylamino or 3-nitro-4-N,N-dimethyl-aminophenyl, 2,3,4-, 2,3,5-, 2,3,6-, 2,4,6- or 3,4,5-trichlorophenyl, 2,4,6-tri-tert-butylphenyl, furthermore preferably 2-nitro-4-(trifluoromethyl)phenyl, 3,5-di-(trifluoromethyl)phenyl, 2,5-dimethylphenyl, 2-hydroxy-3, 5-dichlorophenyl, 2-fluoro-5- or 4-fluoro-3-(trifluoromethyl)phenyl, 4-chloro-2- or 4-chloro-3-(trifluoromethyl), 2-chloro-4- or 2-chloro-5-(trifluoromethyl)phenyl, 4-bromo-2- or 4-bromo-3-(trifluoromethyl)phenyl, p-iodophenyl, 2-nitro-4-methoxyphenyl, 2,5-dimethoxy-4-nitrophenyl, 2-methyl-5-nitrophenyl, 2,4-dimethyl-3-nitrophenyl, 3,6-dichloro-4-aminophenyl, 4-fluoro-3-chlorophenyl, 4-fluoro-3,5-dimethylphenyl, 2-fluoro-4-bromophenyl, 2,5-difluoro-4-bromophenyl, 2,4-dichloro-5-methylphenyl, 3-bromo-6-methoxyphenyl, 3-chloro-6-methoxyphenyl, 2-methoxy-5-methylphenyl, 2,4,6-triisopropylphenyl, naphthyl or 5-dimethylamino-1-naphthyl (dansyl).

Het is preferably 2- or 3-furyl, 2- or 3-thienyl, 1-,2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or 5-yl, 1,3, 4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4-H-thiopyranyl, 3- or 4-pyridazinyl, pyrazinyl, 2-, 3-, 4-, 5- 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzoisoxazolyl, 2-, 4-, 5-, 6- or 7-benzothiazolyl, 2-, 4-, 5-, 6- or 7-benzisothiazolyl, 4-, 5-, 6- or 7-benzo-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-quinolinyl, 2-, 4-, 5-, 6-, 7- or 8-quinazolinyl. The heterocyclic radicals can also be partially or completely hydrogenated. Het can thus, for example, also be 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3 or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl.

The radical $R^2$ is preferably Ar, 2,3-methylenedioxyphenyl, 3,4-methylenedioxyphenyl, 2,3-ethylenedioxyphenyl, 3,4-ethylenedioxyphenyl, 2,3-(2-oxomethylenedioxy)phenyl, 2,3-, 2,4-, 2,5-, 2,6-, 3,4- or 3,5-(difluoromethoxy) (carboxymethoxy)phenyl, 2,3-, 2,4-, 2,5-, 2,6-, 3-4- or 3,5-methoxy-(carboxymethoxy)phenyl, 2,3-, 2,4-, 2,5-, 2,6-, 3,4- or 3,5-hydroxy-(carboxymethoxy) phenyl.

$R^2$ is furthermore preferably 2,3-dihydrobenzofuranyl, 2,3-dihydro-2-oxofuranyl, furthermore preferably 2,1,3-benzothiadiazol-4- or -5-yl or 2,1,3-benzoxadiazol -5-yl.

The radical $R^3$ is preferably carbomethoxy, carboethoxy, carbopropoxy, carbobutoxy, carbobenzyloxy, furthermore cyano, 1H-tetrazol-5-yl or carboxyl, but particularly preferably is phenylsulfonamidocarbonyl or 4-alkyl-phenylsulfonamidocarbonyl.

It applies to the entire invention that all radicals which occur repeatedly, such as, for example, $R^4$, $R^{4'}$ or $R^5$ can be identical or different, i.e. are independent of one another. If, for example, Y is —C($R^4R^{4'}$)C($R^4R^{4'}$)—, the two C atoms can also be identically or differently substituted.

Accordingly, the invention relates in particular to those compounds of the formula I in which at least one of the radicals mentioned has one of the preferred meanings indicated above. Some preferred groups of compounds can be expressed by the following subformulae Ia to Ih, which correspond to the formula I and in which the radicals which are not described in greater detail have the meaning indicated in formula I, but in which in Ia Y is —$CH^2$—$CH^2$;
in Ib Y is —CH=CH—;
in Ic Y is —$CH_2$—S—;
in Id Y is —C($R^4R^{4'}$)C($R^4R^{4'}$) and
$R^2$ is a

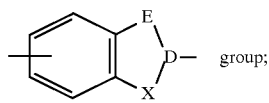 group;

in Ie Y is —$CR^4$=$CR^4$— and
$R^2$ is a

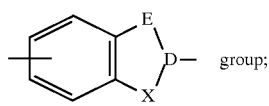 group;

in If Y is —C($R^4R^{4'}$)C($R^4R^{4'}$) and
$R^2$ is Ar;
in Ig Y is —C($R^4R^{4'}$)C($R^4R^{4'}$),
$R^1$ is Ar and
$R^3$ is $CONHSO_2R^5$;
in Ih Y is —C($R^4R^{4'}$)C($R^4R^{4'}$),
$R^1$ is Ar,
$R^2$ is a

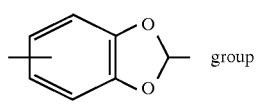 group and
$R^3$ is $CONHSO_2R^5$;

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart; but in particular in EP 0 617 001 A1), namely under reaction conditions which are known and suitable for the reactions mentioned. Use can also be made in this case of variants which are known per se, but not mentioned here in greater detail.

The starting substances, if desired, can also be formed in situ so that they are not isolated from the reaction mixture, but immediately reacted further to give the compounds of the formula I.

Compounds of the formula I can preferably be obtained by reacting compounds of the formula II with compounds of the formula III.

In the compounds of the formula III, Q is preferably Cl, Br, I or a reactive modified OH group such as alkylsulfonyloxy having 1–6 C atoms (preferably methylsulfonyloxy) or arylsulfonyloxy having 6–10 C atoms (preferably phenyl- or p-tolylsulfonyloxy).

The reaction is generally carried out in an inert solvent, in the presence of an acid-binding agent, preferably of an alkali metal or alkaline earth metal hydroxide, carbonate or bicarbonate or of another salt of a weak acid of the alkali metals or alkaline earth metals, preferably of potassium, sodium, calcium or caesium. The addition of an organic base such as triethylamine, dimethylaniline, pyridine or quinoline or of an excess of the phenol component of the formula II or of the alkylation derivative of the formula III may be favourable. The reaction time, depending on the conditions used, is between a few minutes and 14 days and the reaction temperature is between approximately 0° and 150°, normally between 20° and 130°.

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate or mixtures of the solvents mentioned.

The starting compounds of the formulae II and III are known in some cases, but in some cases are alternatively novel. The novel compounds, however, can be prepared by methods known per se. Thus, for example, 6-(2,4-dimethoxyphenyl)-2,3-dihydropyridazin-3-one can be obtained by reaction of 4-(2,4-dimethoxyphenyl)-4-oxobutanoic acid with hydrazine and subsequent reaction of the 6-(2,4-dimethoxyphenol)-2,3,4,5-tetrahydropyridazin-3-one formed with bromine. Furthermore, for example, methyl benzo[1,3]dioxol-5-yl-bromoacetate can be obtained by reaction of methyl benzo[1,3]-dioxol-5-ylhydroxyacetate with phosphorus tribromide. This reaction is expediently carried out at temperatures between 0° and approximately 200°; preferably between 30° and 80°. Suitable inert solvents are those already mentioned above.

It is furthermore possible to convert a compound of the formula I into another compound of the formula I by converting one or more radicals $R^1$,$R^2$ and/or $R^3$ into one or more other radicals $R^1$,$R^2$ and/or $R^3$, e.g. by hydrolysing an ester group to a carboxyl group and/or converting a carboxyl group into a sulfonamidocarbonyl group.

Furthermore, free amino groups can be acylated in the customary manner using a sulfonyl chloride or sulfonic anhydride or alkylated using an unsubstituted or substituted alkyl halide, expediently in an inert solvent such as dichloromethane or THF and/or in the presence of a base such as triethylamine or pyridine at temperatures between −60° and +30°.

If desired, a functionally modified amino and/or hydroxyl group in a compound of the formula I can be liberated by solvolysis or hydrogenolysis according to customary methods. Thus, for example, a compound of the formula I which contains an NHCOR or a COOR group can be converted into the corresponding compound of the formula I which, instead of this, contains an $NH_2$- or an HOOC-group. $COOR^4$ groups can be hydrolysed, for example, using NaOH or KOH in water, water-THF or water-dioxane at temperatures between 0° and 100°.

A base of the formula I can be converted into the associated acid addition salt using an acid, for example by reaction of equivalent amounts of the base and of the acid in an inert solvent such as ethanol and subsequent evaporation. Suitable acids for this reaction are particularly those which give physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, furthermore organic acids, in particular aliphatic, alicyclic, araliphatic, aromatic or hetercyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, and laurylsulfuric acid. Salts with physiologically unacceptable acids, e.g. picrates, can be used for the isolation and/or purification of the compounds of the formula I.

On the other hand, compounds of the formula I can be converted using bases (e.g. sodium or potassium hydroxide or carbonate) into the corresponding metal salts, in particular alkali metal salts or alkaline earth metal salts, or into the corresponding ammonium salts.

The compounds of the formula I can contain one or more centers of asymmetry. In this case, they usually exist in racemic form. Racemates which are obtained can be separated into their enantiomers mechanically or chemically by methods known per se. Preferably, diastereomers are formed from the racemic mixture by reaction with an optically active resolving agent.

Of course, it is also possible to obtain optically active compounds of the formula I by the methods described above by using starting substances which are already optically active.

The present invention furthermore relates to the use of the compounds of the formula I and/or their physiologically acceptable salts for the production of pharmaceutical preparations, in particular in a non-chemical way. In this connection, they can be brought into a suitable dose form together with at least one solid, liquid and/or semiliquid excipient or auxiliary and if appropriate in combination with one or more further active compounds.

The invention furthermore relates to pharmaceutical preparations comprising at least one compound of the formula I and/or one of its physiologically acceptable salts.

These preparations can be used as medicaments in human or veterinary medicine. Suitable excipients are organic or inorganic substances which are suitable for enteral (e.g. oral) administration or parenteral or topical application and do not react with the novel compounds, for example water, vegetable oils, benzyl alcohols, alkylene glycols, polyethylene glycols, glycerol triacetate, gelatine, carbohydrates such as lactose or starch, magnesium stearate, talc and petroleum jelly. Tablets, pills, coated tablets, capsules, powders, granules, syrups, juices or drops are used for oral administration, suppositories are used for rectal administration, solutions, preferably oily or aqueous solutions, furthermore suspensions, emulsions or implants, are used for parenteral administration and ointments, creams or powders are used for topical application. The novel compounds can also be lyophilized and the lyophilizates obtained used, for example, for the production of injection preparations. The preparations indicated can be sterilized and/or contain auxiliaries such as lubricants, preservatives, stabilizers and/or wetting agents, emulsifiers, salts for effecting the osmotic pressure, buffer ,substances, colourants, flavorings and/or one or more further active compounds, e.g. one or more vitamins.

The compounds of the formula I and their physiologically acceptable salts can be used in the control of illnesses, in particular of hypertension and cardiac insufficiency.

In this case, the substances according to the invention are generally preferably administered in doses of between approximately 1 and 500 mg, in particular between 5 and 100 mg per dose unit. The daily dose is preferably between approximately 0.02 and 10 mg/kg of body weight. The specific dose for each patient depends, however, on all sorts of factors, for example on the efficacy of the specific compound employed, on the age, body weight, general state of health, sex, on the diet, on the time and route of administration, on the excretion rate, pharmaceutical substances combination and severity of the particular disorder to which the therapy applies. Oral administration is preferred.

Above and below, all temperatures are indicated in °C. In the following examples, "customary working up" means: if necessary, water is added, if necessary, depending on the constitution of the final product, the mixture is adjusted to a pH of between 2 and 10 and extracted with ethyl acetate or dichloromethane, the organic phase is separated off, dried over sodium sulfate and evaporated, and the residue is purified by chromatography on silica gel and/or by crystallization. Rf values on silica gel: eluent: ethyl acetate/methanol 9:1.

Mass spectrometry (MS): EI (electron impact ionization) $M^+$

FAB (fast atom bombardment) $(M+H)^+$

EXAMPLE 1

3.3 g of caesium carbonate are added to a solution of 1.55 g of 2,3-dihydro-4,6-dimethylpyridazin-3-one (prepared according to F. H. McMillan et al., J. Am.Chem. Soc. 78, 407 (1956)) and 4.52 g of 2-(1,3-benzodioxol-5-yl)-2-bromo-N-(4-isopropylphenylsulfonyl)acetamide in 100 ml of DMF. The mixture is stirred at room temperature for 2 hours and worked up in the customary manner and 2-(1,3-benzodioxol-5-yl)-2-(2,3-dihydro-4,6-dimethylpyridazin-3-on-2-yl)N-(4-isopropylphenylsulfonyl)acetamide is obtained, m.p. 105°.

Analogously, by reaction of methyl benzo[1,3]dioxol-5-ylbromoacetate with 6-phenyl-2,3,4,5-tetrahydropyridazin-3-one 6-(4-methoxyphenyl)-2,3,4,5-tetrahydropyridazin-3-one 6-(4-chlorophenyl)-2,3,4,5-tetrahydropyridazin-3-one 6-(4-ethoxycarbonylphenyl)-2,3,4,5-tetrahydropyridazin-3-one 6-methoxycarbonyl-2,3,4,5-tetrahydropyridazine-3-one 6-(2,5-dimethoxyphenyl)-2,3,4,5-tetrahydropyridazin-3-one 6-(3,4-dimethoxyphenyl)-2,3,4,5-tetrahydropyridazin-3-one 6-(2,4-dimethoxyphenyl)-2,3,4,5-tetrahydropyridazin-3-one 6-(thien-2-yl)-2,3,4,5-tetrahydropyridazin-3-one 6-(furan-2-yl)-2,3,4,5-tetrahydropyridazin-3-one 6-phenyl-4-methyl-2,3,4,5-tetrahydropyridazin-3-one
6-(4-methoxyphenyl)-4-methyl-2,3,4,5-tetrahydropyridazin-3-one
6-(4-chlorophenyl)-4-methyl-2,3,4,5,-tetrahydropyridazin-3-one
6-(4-ethoxycarbonylphenyl)-4-methyl-2,3,4,5-tetrahydropyridazin-3-one
6-(2,5-dimethoxyphenyl)-4-methyl-2,3,4,5-tetrahydropyridazin-3-one
6-(3,4-dimethoxyphenyl)-4-methyl-2,3,4,5-tetrahydropyridazin-3-one
6-(thien-2-yl)-4-methyl-2,3,4,5-tetrahydropyridazin-3-one
6-(furan-2-yl)-4-methyl-2,3,4,5-tetrahydropyridazin-3-one
6-methyl-2,3,4,5-tetrahydropyridazin-3-one
4,4,6-trimethyl-2,3,4,5-tetrahydropyridazin-3-one
4,6-dimethyl-2,3,4,5-tetrahydropyridazin-3-one
6-phenyl-2,3-dihydropyridazin-3-one
5-phenyl-6-methyl-2,3-dihydropyridazin-3-one
4-phenyl-6-methyl-2,3-dihydropyridazin-3-one
6-(4-methoxyphenyl)-2,3-dihydropyridazin-3-one
6-(4-chlorophenyl)-2,3-dihydropyridazin-3-one
6-(4-methoxycarbonylphenyl)-2,3-dihydropyridazin-3-one
6-(2,5-dimethoxyphenyl)-2,3-dihydropyridazin-3-one
6-(3,4-dimethoxyphenyl)-2,3-dihydropyridazin-3-one
6-(thien-2-yl)-2,3-dihydropyridazin-3-one
6-(furan-2-yl)-2,3-dihydropyridazin-3-one
6-phenyl-4-methyl-2,3-dihydropyridazin-3-one
6-(4-methoxyphenyl)-4-methyl-2,3-dihydropyridazin-3-one
6-(4-chlorophenyl)-4-methyl-2,3-dihydropyridazin-3-one
6-(4-chlorophenyl)-5-methyl-2,3-dihydropyridazin-3-one
6-(4-ethoxycarbonylphenyl)-4-methyl-2,3-dihydropyridazin-3-one
6-(2,5-dimethoxyphenyl)-4-methyl-2,3-dihydropyridazin-3-one
6-(3,4-dimethoxyphenyl)-4-methyl-2,3-dihydropyridazin-3-one
6-(thien-2-yl)-4-methyl-2,3-dihydropyridazin-3-one
6- (furan-2-yl)-4-methyl-2,3-dihydropyridazin-3-one
6-methyl-2,3-dihydropyridazin-3-one
6-propyl-2,3-dihydropyridazin-3-one
4,6-dimethyl-2,3-dihydropyridazin-3-one
4-propyl-6- methyl-2,3-dihydropyridazin-3-one
4-ethyl-6-methyl-2,3-dihydropyridazin-3-one
4-methyl-6-ethyl-2,3-dihydropyridazin-3-one
4-methyl-6-propyl-2,3-dihydropyridazin-3-one
5,6-dimethyl-2,3-dihydropyridazin-3-one
4,5,6-trimethyl-2,3-dihydropyridazin-3-one
4-methyl-2,3-dihydropyridazin-3-one
5-(4-methoxyphenyl)-2H-3,6-dihydro-1,3,4-thiadiazin-2-one
5-(3,4-dimethoxyphenyl)-6-ethyl-2H-3,6-dihydro-1,3,4-thiadiazin-2-one
6-(4-methanesulfonylphenyl)-2,3,4,5-tetrahydropyridazin-3-one
2,3-dihydropyridazin-3-one
4-(4-methoxybenzyl)-6-methyl-2,3-dihydropyridazin-3-one
6-tert.-butyl-2,3-dihydropyridazin-3-one
6-cyclopropyl-2,3-dihydropyridazin-3-one
the methyl 2-(1,3-benzodioxol-5-yl)-2-(T-yl)acetates below are obtained,
in which T is
6-phenyl-2,3,4,5-tetrahydropyridazin-3-on-2
6-(4-methoxyphenyl)-2,3,4,5-tetrahydropyridazin-3-on-2
6-(4-chlorophenyl)-2,3,4,5-tetrahydropyridazin-3-on-2
6-(4-ethoxycarbonylphenyl)-2,3,4,5-tetrahydropyridazin-3-on-2
6-methoxycarbonyl-2,3,4,5-tetrahydropyridazine-3-on-2
6-(2,5-dimethoxyphenyl)-2,3,4,5-tetrahydropyridazin-3-on-2
6-(3,4-dimethoxyphenyl)-2,3,4,5-tetrahydropyridazin-3-on-2
6-(2,4-dimethoxyphenyl)-2,3,4,5-tetrahydropyridazin-3-on-2
6-(thien-2-yl)-2,3,4,5-tetrahydropyridazin-3-on-2
6-(furan-2-yl)-2,3,4,5-tetrahydropyridazin-3-on-2
6-phenyl-4-methyl-2,3,4,5-tetrahydropyridazin-3-on-2
6-(4-methoxyphenyl)-4-methyl-2,3,4,5-tetrahydropyridazin-3-on-2
6-(4-chlorophenyl)-4-methyl-2,3,4,5,-tetrahydropyridazin-3-on-2
6-(4-ethoxycarbonylphenyl)-4-methyl-2,3,4,5-tetrahydropyridazin-3-on-2
6-(2,5-dimethoxyphenyl)-4-methyl-2,3,4,5-tetrahydropyridazin-3-on-2
6- (3,4-dimethoxyphenyl)-4-methyl-2,3,4,5-tetrahydropyridazin-3-on-2
6-(thien-2-yl)-4-methyl-2,3,4,5-tetrahydropyridazin-3-on-2
6-(furan-2-yl)-4-methyl-2,3,4,5-tetrahydropyridazin-3-on-2
6-methyl-2,3,4,5-tetrahydropyridazin-3-on-2
4,4,6-trimethyl-2,3,4,5-tetrahydropyridazin-3-on-2
4,6-dimethyl-2,3,4,5-tetrahydropyridazin-3-on-2
6-phenyl-2,3-dihydropyridazin-3-on-2
5-phenyl-6-methyl-2,3-dihydropyridazin-3-one-2
4-phenyl-6-methyl-2,3-dihydropyridazin-3-one-2
6-(4-methoxyphenyl)-2,3-dihydropyridazin-3-on-2
6-(4-chlorophenyl)-2,3-dihydropyridazin-3-on-2
6-(4-methoxycarbonylphenyl)-2,3-dihydropyridazin-3-on-2-6-(2,5-dimethoxyphenyl)-2,3-dihydropyridazin-3-on-2
6-(3,4-dimethoxyphenyl)-2,3-dihydropyridazin-3-on-2
6-(thien-2-yl)-2,3-dihydropyridazin-3-on-2
6-(furan-2-yl)-2,3-dihydropyridazin-3-on-2
6-phenyl-4-methyl-2,3-dihydropyridazin-3-on-2
6-(4-methoxyphenyl)-4-methyl -2,3-dihydropyridazin-3-on-2
6-(4-chlorophenyl)-4-methyl-2,3-dihydropyridazin-3-on-2
6-(4-chlorophenyl)-5-methyl-2,3-dihydropyridazin-3-on-2
6-(4-ethoxycarbonylphenyl)-4-methyl-2,3-dihydropyridazin-3-on-2
6-(2, 5-dimethoxyphenyl) -4-methyl-2,3-dihydropyridazin-3-on-2
6-(3,4-dimethoxyphenyl)-4-methyl-2,3-dihydropyridazin-3-on-2
6-(thien-2-yl)-4-methyl-2,3-dihydropyridazin-3-on-2
6-(furan-2-yl)-4-methyl-2,3-dihydropyridazin-3-on-2

6-methyl-2,3-dihydropyridazin-3-on-2
6-propyl-2,3-dihydropyridazin-3-one-2
4,6-dimethyl-2,3-dihydropyridazin-3-on-2, EI 316
4-propyl-6-methyl-2,3-dihydropyridazin-3-on-2
4-ethyl-6-methyl-2,3-dihydropyridazin-3-one-2
4-methyl-6-ethyl-2,3-dihydropyridazin-3-one-2
4-methyl-6-propyl-2,3-dihydropyridazin-3-on-2
5,6-dimethyl-2,3-dihydropyridazin-3-on-2
4,5,6-trimethyl-2,3-dihydropyridazin-3-on-2
4-methyl-2,3-dihydropyridazin-3-on-2
5-(4-methoxyphenyl)-2H-3,6-dihydro-1,3,4-thiadiazin-2-on-3
5-(3,4-dimethoxyphenyl)-6-ethyl-2H-3,6-dihydro-1,3,4-thiadiazin-2-on-3
6-(4-methanesulfonylphenyl)-2,3,4,5-tetrahydropyridazin-3-on-2
2,3-dihydropyridazin-3-one-2
4-(4-methoxybenzyl)-6-methyl-2,3-dihydropyridazin-3-one-2
6-tert.-butyl-2,3-dihydropyridazin-3-one-2
6-cyclopropyl-2,3-dihydropyridazin-3-one-2.

EXAMPLE 2

A solution of 2.24 g of methyl 2-(1,3-benzodioxol-5-yl)-2-(4,6-dimethyl-2,3-dihydropyridazin-3-on-2-yl)-acetate in 20 ml of methanol is treated with 7.08 ml of 1N sodium hydroxide solution and the mixture is stirred at room temperature for 18 hours. It is worked up in the customary manner and 2-(1,3-benzodioxol-5-yl)-2-(4,6-dimethyl-2,3-dihydropyridazin-3-on-2-yl)acetic acid is obtained, m.p. 165°, EI 302.

Analogously, by hydrolysis of the methyl 2-(1,3-benzodioxol-5-yl)-2-(T-yl)acetates below, in which T is
6-phenyl-2,3,4,5-tetrahydropyridazin-3-on-2
6-(4-methoxyphenyl)-2,3,4,5-tetrahydropyridazin-3-on-2
6-(4-chlorophenyl)-2,3,4,5-tetrahydropyridazin-3-on-2
6-(4-ethoxycarbonylphenyl)-2,3,4,5-tetrahydropyridazin-3-on-2
6-methoxycarbonyl-2,3,4,5-tetrahydropyridazine-3-on-2
6-(2,5-dimethoxyphenyl)-2,3,4,5-tetrahydropyridazin-3-on-2
6-(3,4-dimethoxyphenyl)-2,3,4,5-tetrahydropyridazin-3-on-2
6-(2,4-dimethoxyphenyl)-2,3,4,5-tetrahydropyridazin-3-on-2
6-(thien-2-yl)-2,3,4,5-tetrahydropyridazin-3-on-2
6-(furan-2-yl)-2,3,4,5-tetrahydropyridazin-3-on-2
6-phenyl-4-methyl-2,3,4,5-tetrahydropyridazin-3-on-2
6-(4-methoxyphenyl)-4-methyl-2,3,4,5-tetrahydropyridazin-3-on-2
6-(4-chlorophenyl)-4-methyl-2,3,4,5,-tetrahydropyridazin-3-on-2
6-(4-ethoxycarbonylphenyl)-4-methyl-2,3,4,5-tetrahydropyridazin-3-on-2
6-(2,5-dimethoxyphenyl)-4-methyl-2,3,4,5-tetrahydropyridazin-3-on-2
6-(3,4-dimethoxyphenyl)-4-methyl-2,3,4,5-tetrahydropyridazin-3-on-2
6-(thien-2-yl)-4-methyl-2,3,4,5-tetrahydropyridazin-3-on-2
6-(furan-2-yl)-4-methyl-2,3,4,5-tetrahydropyridazin-3-on-2
6-methyl-2,3,4,5-tetrahydropyridazin-3-on-2
4,4,6-trimethyl-2,3,4,5-tetrahydropyridazin-3-on-2
4,6-dimethyl-2,3,4,5-tetrahydropyridazin-3-on-2
6-phenyl-2,3-dihydropyridazin-3-on-2
5-phenyl-6-methyl-2,3-dihydropyridazin-3-one-2
4-phenyl-6-methyl-2,3-dihydropyridazin-3-one-2
6-(4-methoxyphenyl)-2,3-dihydropyridazin-3-on-2
6-(4-chlorophenyl)-2,3-dihydropyridazin-3-on-2
6-(4-methoxycarbonylphenyl)-2,3-dihydropyridazin-3-on-2
6-(2,5-dimethoxyphenyl)-2,3-dihydropyridazin-3-on-2
6-(3,4-dimethoxyphenyl)-2,3-dihydropyridazin-3-on-2
6-(thien-2-yl)-2,3-dihydropyridazin-3-on-2
6-(furan-2-yl)-2,3-dihydropyridazin-3-on-2
6-phenyl-4-methyl-2,3-dihydropyridazin-3-on-2
6-(4-methoxyphenyl)-4-methyl-2,3-dihydropyridazin-3-on-2
6-(4-chlorophenyl)-4-methyl-2,3-dihydropyridazin-3-on-2
6-(4-chlorophenyl)-5-methyl-2,3-dihydropyridazin-3-on-2
6-(4-ethoxycarbonylphenyl)-4-methyl-2,3-dihydropyridazin-3-on-2
6-(2,5-dimethoxyphenyl)-4-methyl-2,3-dihydropyridazin-3-on-2
6-(3,4-dimethoxyphenyl)-4-methyl-2,3-dihydropyridazin-3-on-2
6-(thien-2-yl)-4-methyl-2,3-dihydropyridazin-3-on-2
6-(furan-2-yl)-4-methyl-2,3-dihydropyridazin-3-on-2
6-methyl-2,3-dihydropyridazin-3-on-2
6-propyl-2,3-dihydropyridazin-3-one-2
4-propyl-6-methyl-2,3-dihydropyridazin-3-on-2
4-ethyl-6-methyl-2,3-dihydropyridazin-3-one-2
4-methyl-6-ethyl-2,3-dihydropyridazin-3-one-2
4-methyl-6-propyl-2,3-dihydropyridazin-3-on-2
5,6-dimethyl-2,3-dihydropyridazin-3-on-2
4,5,6-trimethyl-2,3-dihydropyridazin-3-on-2
4-methyl-2,3-dihydropyridazin-3-on-2
5-(4-methoxyphenyl)-2H-3,6-dihydro-1,3,4-thiadiazin-2-on-3
5-(3,4-dimethoxyphenyl)-6-ethyl-2H-3,6-dihydro-1,3,4-thiadiazin-2-on-3
6-(4-methanesulfonylphenyl)-2,3,4,5-tetrahydropyridazin-3-on-2
2,3-dihydropyridazin-3-one-2
4-(4-methoxybenzyl)-6-methyl-2,3-dihydropyridazin-3-one-2
6-tert.-butyl-2,3-dihydropyridazin-3-one-2
6-cyclopropyl-2,3-dihydropyridazin-3-one-2, the 2-(1,3-benzodioxol-5-yl)-2-(T-yl)acetic acids below are obtained, in which T is
6-phenyl-2,3,4,5-tetrahydropyridazin-3-on-2
6-(4-methoxyphenyl)-2,3,4,5-tetrahydropyridazin-3-on-2, m.p. 181°
6-(4-chlorophenyl)-2,3,4,5-tetrahydropyridazin-3-on-2, m.p. 168°
6-(4-carboxyphenyl)-2,3,4,5-tetrahydropyridazin-3-on-2, m.p. 184°
6-carboxy-2,3,4,5-tetrahydropyridazine-3-one, m.p. 178°
6-(2,5-dimethoxyphenyl)-2,3,4,5-tetrahydropyridazin-3-on-2, m.p. 149°
6-(3,4-dimethoxyphenyl)-2,3,4,5-tetrahydropyridazin-3-on-2, m.p. decomposition, FAB 413
6-(2,4-dimethoxyphenyl)-2,3,4,5-tetrahydropyridazin-3-one
6-(thien-2-yl)-2,3,4,5-tetrahydropyridazin-3-on-2, m.p. 110°

6-(furan-2-yl)-2,3,4,5-tetrahydropyridazin-3-on-2, FAB 343
6-phenyl-4-methyl-2,3,4,5-tetrahydropyridazin-3-on-2, diastereomer mixture, FAB 367
6-(4-methoxyphenyl)-4-methyl-2,3,4,5-tetrahydropyridazin-3-on-2
6-(4-chlorophenyl)-4-methyl-2,3,4,5,-tetrahydropyridazin-3-on-2
6-(4-carboxyphenyl)-4-methyl-2,3,4,5-tetrahydropyridazin-3-on-2
6-(2,5-dimethoxyphenyl)-4-methyl-2,3,4,5-tetrahydropyridazin-3-on-2
6-(3,4-dimethoxyphenyl)-4-methyl-2,3,4,5-tetrahydropyridazin-3-on-2
6-(thien-2-yl)-4-methyl-2,3,4,5-tetrahydropyridazin-3-on-2
6-(furan-2-yl)-4-methyl-2,3,4,5-tetrahydropyridazin-3-on-2
6-methyl-2,3,4,5-tetrahydropyridazin-3-on-2
4,4,6-trimethyl-2,3,4,5-tetrahydropyridazin-3-on-2
4,6-dimethyl-2,3,4,5-tetrahydropyridazin-3-on-2
6-phenyl-2,3-dihydropyridazin-3-on-2
5-phenyl-6-methyl-2,3-dihydropyridazin-3-one-2
4-phenyl-6-methyl-2,3-dihydropyridazin-3-one-2
6-(4-methoxyphenyl)-2,3-dihydropyridazin-3-on-2, m.p. 164°
6-(4-chlorophenyl)-2,3-dihydropyridazin-3-on-2
6-(4-carboxyphenyl)-2,3-dihydropyridazin-3-on-2
6-(2,5-dimethoxyphenyl)-2,3-dihydropyridazin-3-on-2
6- (3,4-dimethoxyphenyl)-2,3-dihydropyridazin-3-on-2
6-(thien-2-yl)-2,3-dihydropyridazin-3-on-2
6-(furan-2-yl)-2,3-dihydropyridazin-3-on-2
6-phenyl-4-methyl-2,3-dihydropyridazin-3-on-2, m.p. 125° C.
6-(4-methoxyphenyl)-4-methyl-2,3-dihydropyridazin-3-on-2, FAB 395
6-(4-chlorophenyl)-4-methyl-2,3-dihydropyridazin-3-on-2
6-(4-chlorophenyl)-5-methyl-2,3-dihydropyridazin-3-on-2 m.p. 171°
6-(4-carboxyphenyl)-4-methyl-2,3-dihydropyridazin-3-on-2
6-(2,5-dimethoxyphenyl)-4-methyl-2,3-dihydropyridazin-3-on-2
6-(3,4-dimethoxyphenyl)-4-methyl-2,3-dihydropyridazin-3-on-2
6-(thien-2-yl)-4-methyl-2,3-dihydropyridazin-3-on-2
6-(furan-2-yl)-4-methyl-2,3-dihydropyridazin-3-on-2
6-methyl-2,3-dihydropyridazin-3-on-2, m.p. 213°
6-propyl-2,3-dihydropyridazin-3-one-2, m.p. 177°
4-propyl-6-methyl-2,3-dihydropyridazin-3-on-2, EI 330
4-ethyl-6-methyl-2,3-dihydropyridazin-3-one-2, m.p. 159°
4-methyl-6-ethyl-2,3-dihydropyridazin-3-one-2, m.p. 106°
4-methyl-6-propyl-2,3-dihydropyridazin-3-on-2, m.p. 225°
5,6-dimethyl-2,3-dihydropyridazin-3-on-2, m.p. 199°
4,5,6-trimethyl-2,3-dihydropyridazin-3-on-2, m.p. 184°
4-methyl-2,3-dihydropyridazin-3-on-2
5-(4-methoxyphenyl)-2H-3,6-dihydro-1,3,4-thiadiazin-2-on-3, m.p. 139°
5-(3,4-dimethoxyphenyl)-6-ethyl-2H-3,6-dihydro-1,3,4-thiadiazin-2-on-3, sodium salt, m.p. 216° b  6-(4-methanesulfonylphenyl)-2,3,4,5-tetrahydropyridazin-3-on-2
2,3-dihydropyridazin-3-one-2, FAB 275
4-(4-methoxybenzyl)-6-methyl-2,3-dihydropyridazin-3-one-2, FAB 409
6-tert.-butyl-2,3-dihydropyridazin-3-one-2, m.p. 179°
6-cyclopropyl-2,3-dihydropyridazin-3-one-2, m.p. 204°.

EXAMPLE 3

A solution of 0.8 g of 2-(1,3-benzodioxol-5-yl)-2-(4,6-dimethyl-2,3-dihydropyridazin-3-on-2-yl)acetic acid and 0.64 g of carbonyldiimidazole in 50 ml of THF is heated at 60° for 2 hours. 0.79 g of 4-isopropylbenzenesulfonamide and 0.59 g of 1, 8-diazabicyclo[5.4.0]undec-7-ene are then added and the mixture is stirred at this temperature for a further 1 hour. After customary working up, 2-(1,3-benzodioxol-5-yl)-2-(4,6-dimethyl-2,3-dihydropyridazin-3-on-2-yl) N-(4-isopropylphenylsulfonyl)acetamide is obtained, m.p. 105°.

Analogously, by reaction of 4-isopropylbenzenesulfonamide with the 2-(1,3-benzodioxol-5-yl)-2-(T-yl)acetic acids below,
    in which T is
        6-phenyl-2,3,4,5-tetrahydropyridazin-3-on-2
        6-(4-methoxyphenyl)-2,3,4,5-tetrahydropyridazin-3-on-2
        6-(4-chlorophenyl)-2,3,4,5-tetrahydropyridazin-3-on-2
        6-(4-carboxyphenyl)-2,3,4,5-tetrahydropyridazin-3-on-2
        6-carboxy-2,3,4,5-tetrahydropyridazine-3-on-2
        6-(2,5-dimethoxyphenyl)-2,3,4,5-tetrahydropyridazin-3-on-2
        6-(3,4-dimethoxyphenyl)-2,3,4,5-tetrahydropyridazin-3-on-2
        6-(2,4-dimethoxyphenyl)-2,3,4,5-tetrahydropyridazin-3-one
        6-(thien-2-yl)-2,3,4,5-tetrahydropyridazin-3-on-2
        6-(furan-2-yl)-2,3,4,5-tetrahydropyridazin-3-on-2
        6-phenyl-4-methyl-2,3,4,5-tetrahydropyridazin-3-on-2
        6-(4-methoxyphenyl)-4-methyl-2,3,4,5-tetrahydropyridazin-3-on-2
        6-(4-chlorophenyl)-4-methyl-2,3,4,5,-tetrahydropyridazin-3-on-2
        6-(4-carboxyphenyl)-4-methyl-2,3,4,5-tetrahydropyridazin-3-on-2
        6-(2,5-dimethoxyphenyl)-4-methyl-2,3,4,5-tetrahydropyridazin-3-on-2
        6-(3,4-dimethoxyphenyl)-4-methyl-2,3,4,5-tetrahydropyridazin-3-on-2
        6-(thien-2-yl)-4-methyl-2,3,4,5-tetrahydropyridazin-3-on-2
        6-(furan-2-yl)-4-methyl-2,3,4,5-tetrahydropyridazin-3-on-2
        6-methyl-2,3,4,5-tetrahydropyridazin-3-on-2
        4,4,6-trimethyl-2,3,4,5-tetrahydropyridazin-3-on-2
        4,6-dimethyl-2,3,4,5-tetrahydropyridazin-3-on-2
        6-phenyl-2,3-dihydropyridazin-3-on-2
        5-phenyl-6-methyl-2,3-dihydropyridazin-3-one-2
        6-(4-methoxyphenyl)-2,3-dihydropyridazin-3-on-2
        6-(4-chlorophenyl)-2,3-dihydropyridazin-3-on-2
        6-(4-carbonylphenyl)-2,3-dihydropyridazin-3-on-2
        6-(2,5-dimethoxyphenyl)-2,3-dihydropyridazin-3-on-2
        6-(3,4-dimethoxyphenyl)-2,3-dihydropyridazin-3-on-2
        6-(thien-2-y) -2,3-dihydropyridazin-3-on-2
        6-(furan-2-yl)-2,3-dihydropyridazin-3-on-2
        6-phenyl-4-methyl-2,3-dihydropyridazin-3-on-2

6-(4-methoxyphenyl)-4-methyl-2,3-dihydropyridazin-3-on-2
6-(4-chlorophenyl)-4-methyl-2,3-dihydropyridazin-3-on-2
6-(4-chlorophenyl)-5-methyl-2,3-dihydropyridazin-3-on-2
6-(4-carboxylphenyl)-4-methyl-2,3-dihydropyridazin-3-on-2
6-(2,5-dimethoxyphenyl)-4-methyl-2,3-dihydropyridazin-3-on-2
6-(3,4-dimethoxyphenyl)-4-methyl-2,3-dihydropyridazin-3-on-2
6-(thien-2-yl)-4-methyl-2,3-dihydropyridazin-3-on-2
6-(furan-2-yl)-4-methyl-2,3-dihydropyridazin-3-on-2
6-methyl-2,3-dihydropyridazin-3-on-2
6-propyl-2,3-dihydropyridazin-3-one-2
4-propyl-6-methyl-2,3-dihydropyridazin-3-on-2
4-ethyl-6-methyl-2,3-dihydropyridazin-3-one-2
4-methyl-6-propyl-2,3-dihydropyridazin-3-on-2
5,6-dimethyl-2,3-dihydropyridazin-3-on-2
4,5,6-trimethyl-2,3-dihydropyridazin-3-on-2
4-methyl-2,3-dihydropyridazin-3-on-2
5-(4-methoxyphenyl)-2H-3,6-dihydro-1,3,4-thiadiazin-2-on-3
5-(3,4-dimethoxyphenyl)-6-ethyl-2H-3,6-dihydro-1,3,4-thiadiazin-2-on-3
4,6-dimethyl-2,3-dihydropyridazin-3-one-2
4-(4-methoxybenzyl)-6-methyl-2,3-dihydropyridazin-3-one-2
6-tert.-butyl-2,3-dihydropyridazin-3-one-2
6-cyclopropyl-2,3-dihydropyridazin-3-one-2, the following 2-(1,3-benzodioxol-5-yl)-2-(T-yl)N-(4-isopropylphenylsulfonyl)acetamides are obtained,
in which T is
6-phenyl-2,3,4,5-tetrahydropyridazin-3-on-2, m.p. 187°
6-(4-methoxyphenyl)-2,3,4,5-tetrahydropyridazin-3-on-2, FAB 564
6-(4-chlorophenyl)-2,3,4,5-tetrahydropyridazin-3-on-2, FAB 568
6-(4-carboxyphenyl)-2,3,4,5-tetrahydropyridazin-3-on-2
6-carboxy-2,3,4,5-tetrahydropyridazine-3-one
6-(2,5-dimethoxyphenyl)-2,3,4,5-tetrahydropyridazin-3-on-2, m.p. 187°
6-(3,4-dimethoxyphenyl)-2,3,4,5-tetrahydropyridazin-3-on-2, m.p. 223°
6-(2,4-dimethoxyphenyl)-2,3,4,5-tetrahydropyridazin-3-one, FAB 594
6-(thien-2-yl)-2,3,4,5-tetrahydropyridazin-3-on-2, m.p. 190°
6-(furan-2-yl)-2,3,4,5-tetrahydropyridazin-3-on-2
6-phenyl-4-methyl-2,3,4,5-tetrahydropyridazin-3-on-2
6-(4-methoxyphenyl)-4-methyl-2,3,4,5-tetrahydropyridazin-3-on-2
6-(4-chlorophenyl)-4-methyl-2,3,4,5,-tetrahydropyridazin-3-on-2
6-(4-carboxyphenyl)-4-methyl-2,3,4,5-tetrahydropyridazin-3-on-2
6-(2,5-dimethoxyphenyl)-4-methyl-2,3,4,5-tetrahydropyridazin-3-on-2
6-(3,4-dimethoxyphenyl)-4-methyl-2,3,4,5-tetrahydropyridazin-3-on-2
6-(thien-2-yl)-4-methyl-2,3,4,5-tetrahydropyridazin-3-on-2
6-(furan-2-yl)-4-methyl-2,3,4,5-tetrahydropyridazin-3-on-2
6-methyl-2,3,4,5-tetrahydropyridazin-3-on-2, FAB 470
4,4,6-trimethyl-2,3,4,5-tetrahydropyridazin-3-on-2
4,6-dimethyl-2,3,4,5-tetrahydropyridazin-3-on-2
6-phenyl-2,3-dihydropyridazin-3-on-2
5-phenyl-6-methyl-2,3-dihydropyridazin-3-one-2
6-(4-methoxyphenyl)-2,3-dihydropyridazin-3-on-2, m.p. 164°
6-(4-chlorophenyl)-2,3-dihydropyridazin-3-on-2
6-(4-carboxyphenyl)-2,3-dihydropyridazin-3-on-2
6-(2,5-dimethoxyphenyl)-2,3-dihydropyridazin-3-on-2
6-(3,4-dimethoxyphenyl)-2,3-dihydropyridazin-3-on-2
6-(thien-2-yl)-2,3-dihydropyridazin-3-on-2
6-(furan-2-yl)-2,3-dihydropyridazin-3-on-2
6-phenyl-4-methyl-2,3-dihydropyridazin-3-on-2, m.p. 196°
6-(4-methoxyphenyl)-4-methyl-2,3-dihydropyridazin-3-on-2, FAB 579
6-(4-chlorophenyl)-4-methyl-2,3-dihydropyridazin-3-on-2
6-(4-chlorophenyl)-5-methyl-2,3-dihydropyridazin-3-on-2
6-(4-carboxyphenyl)-4-methyl-2,3-dihydropyridazin-3-on-2
6-(2,5-dimethoxyphenyl)-4-methyl-2,3-dihydropyridazin-3-on-2
6-(3,4-dimethoxyphenyl)-4-methyl-2,3-dihydropyridazin-3-on-2
6-(thien-2-yl)-4-methyl-2,3-dihydropyridazin-3-on-2
6-(furan-2-yl)-4-methyl-2,3-dihydropyridazin-3-on-2
6-methyl-2,3-dihydropyridazin-3-on-2, m.p.>250° (decomposition)
6-propyl-2,3-dihydropyridazin-3-one-2, FAB 498
4-propyl-6-methyl-2,3-dihydropyridazin-3-on-2
4-ethyl-6-methyl-2,3-dihydropyridazin-3-one-2, m.p. 198°
4-methyl-6-propyl-2,3-dihydropyridazin-3-on-2, m.p. 210°
5,6-dimethyl-2,3-dihydropyridazin-3-on-2, m.p. 194°
4,5,6-trimethyl-2,3-dihydropyridazin-3-on-2
4-methyl-2,3-dihydropyridazin-3-on-2
5-(4-methoxyphenyl)-2H-3,6-dihydro-1,3,4-thiadiazin-2-on-3
5-(3,4-dimethoxyphenyl)-6-ethyl-2H-3,6-dihydro-1,3,4-thiadiazin-2-on-3
4,6-dimethyl-2,3-dihydropyridazin-3-one-2, FAB 484; potassium salt FAB 522
4-(4-methoxybenzyl)-6-methyl-2,3-dihydropyridazin-3-one-2, FAB 590
6-tert.-butyl-2,3-dihydropyridazin-3-one-2, FAB 511
6-cyclopropyl-2,3-dihydropyridazin-3-one-2, FAB 496.

Analogously, by reaction of 4-tert-butylbenzenesulfonamide with the 2-(1,3-benzodioxol-5-yl)-2-(T-yl)-acetic acids below,
in which T is
6-phenyl-2,3,4,5-tetrahydropyridazin-3-on-2
6-(4-methoxyphenyl)-2,3,4,5-tetrahydropyridazin-3-on-2
6-(4-chlorophenyl)-2,3,4,5-tetrahydropyridazin-3-on-2
6-(4-carboxyphenyl)-2,3,4,5-tetrahydropyridazin-3-on-2
6-carboxy-2,3,4,5-tetrahydropyridazine-3-on-2
6-(2,5-dimethoxyphenyl)-2,3,4,5-tetrahydropyridazin-3-on-2
6-(3,4-dimethoxyphenyl)-2,3,4,5-tetrahydropyridazin-3-on-2
6-(2,4-dimethoxyphenyl)-2,3,4,5-tetrahydropyridazin-3-one 6-(thien-2-yl)-2,3,4,5-tetrahydropyridazin-3-on-2
6-phenyl-4-methyl-2,3,4,5-tetrahydropyridazin-3-on-2
6-(4-methoxyphenyl)-4-methyl-2,3,4,5-tetrahydropyridazin-3-on-2
6-(4-chlorophenyl)-4-methyl-2,3,4,5,-tetrahydropyridazin-3-on-2
6-(4-carboxyphenyl)-4-methyl-2,3,4,5-tetrahydropyridazin-3-on-2
6-(2,5-dimethoxyphenyl)-4-methyl-2,3,4,5-tetrahydropyridazin-3-on-2
6-(3,4-dimethoxyphenyl)-4-methyl-2,3,4,5-tetrahydropyridazin-3-on-2
6-(thien-2-yl)-4-methyl-2,3,4,5-tetrahydropyridazin-3-on-2
6-methyl-2,3,4,5-tetrahydropyridazin-3-on-2
4,4,6-trimethyl-2,3,4,5-tetrahydropyridazin-3-on-2
4,6-dimethyl-2,3,4,5-tetrahydropyridazin-3-on-2
6-phenyl-2,3-dihydropyridazin-3-on-2
6-(4-methoxyphenyl)-2,3-dihydropyridazin-3-on-2
6-(4-chlorophenyl)-2,3-dihydropyridazin-3-on-2
6-(4-carboxyphenyl)-2,3-dihydropyridazin-3-on-2
6-(2,5-dimethoxyphenyl)-2,3-dihydropyridazin-3-on-2
6-(3,4-dimethoxyphenyl)-2,3-dihydropyridazin-3-on-2
6-(thien-2-yl)-2,3-dihydropyridazin-3-on-2
6-phenyl-4-methyl-2,3-dihydropyridazin-3-on-2
6-(4-methoxyphenyl)-4-methyl-2,3-dihydropyridazin-3-on-2
6-(4-chlorophenyl)-4-methyl-2,3-dihydropyridazin-3-on-2
6-(4-chlorophenyl)-5-methyl-2,3-dihydropyridazin-3-on-2
6-(4-carboxyphenyl)-4-methyl-2,3-dihydropyridazin-3-on-2
6-(2,5-dimethoxyphenyl)-4-methyl-2,3-dihydropyridazin-3-on-2
6-(3,4-dimethoxyphenyl)-4-methyl-2,3-dihydropyridazin-3-on-2
6-(thien-2-yl)-4-methyl-2,3-dihydropyridazin-3-on-2
6-methyl-2,3-dihydropyridazin-3-on-2
4,6-dimethyl-2,3-dihydropyridazin-3-on-2
4-propyl-6-methyl-2,3-dihydropyridazin-3-on-2
4-methyl-6-propyl-2,3-dihydropyridazin-3-on-2
5,6-dimethyl-2,3-dihydropyridazin-3-on-2
4,5,6-trimethyl-2,3-dihydropyridazin-3-on-2
4-methyl- 2,3-dihydropyridazin-3-on-2
5-(4-methoxyphenyl)-2H-3,6-dihydro-1,3,4-thiadiazin-2-on-3
5-(3,4-dimethoxyphenyl)-6-ethyl-2H-3, 6-dihydro-1,3,4-thiadiazin-2-on-3, the following 2-(1,3-benzodioxol-5-yl)-2-(T-yl)N-(4-tert-butylsulfonyl)acetamides are obtained,
in which T is
6-phenyl-2,3,4,5-tetrahydropyridazin-3-on-2
6-(4-methoxyphenyl)-2,3,4,5-tetrahydropyridazin-3-on-2, m.p. 213°
6-(4-chlorophenyl)-2,3,4,5-tetrahydropyridazin-3-on-2
6-(4-carboxyphenyl)-2,3,4,5-tetrahydropyridazin-3-on-2
6-carboxy-2,3,4,5-tetrahydropyridazine-3-on-2
6-(2,5-dimethoxyphenyl)-2,3,4,5-tetrahydropyridazin-3-on-2
6-(3,4-dimethoxyphenyl)-2,3,4,5-tetrahydropyridazin-3-on-2
6-(2,4-dimethoxyphenyl)-2,3,4,5-tetrahydropyridazin-3-one
6-(thien-2-yl)-2,3,4,5-tetrahydropyridazin-3-on-2
6-phenyl-4-methyl-2,3,4,5-tetrahydropyridazin-3-on-2
6-(4-methoxyphenyl)-4-methyl-2,3,4,5-tetrahydropyridazin-3-on-2
6-(4-chlorophenyl)-4-methyl-2,3,4,5,-tetrahydropyridazin-3-on-2
6-(4-carboxyphenyl)-4-methyl-2,3,4,5-tetrahydropyridazin-3-on-2
6-(2,5-dimethoxyphenyl)-4-methyl-2,3,4,5-tetrahydropyridazin-3-on-2
6-(3,4-dimethoxyphenyl)-4-methyl-2,3,4,5-tetrahydropyridazin-3-on-2
6-(thien-2-yl)-4-methyl-2,3,4,5-tetrahydropyridazin-3-on-2
6-methyl-2,3,4,5-tetrahydropyridazin-3-on-2
4,4,6-trimethyl-2,3,4,5-tetrahydropyridazin-3-on-2
4,6-dimethyl-2,3,4,5-tetrahydropyridazin-3-on-2
6-phenyl-2,3-dihydropyridazin-3-on-2
6-(4-methoxyphenyl)-2,3-dihydropyridazin-3-on-2
6-(4-chlorophenyl)-2,3-dihydropyridazin-3-on-2
6-(4-carboxyphenyl)-2,3-dihydropyridazin-3-on-2
6-(2,5-dimethoxyphenyl)-2,3-dihydropyridazin-3-on-2
6-(3,4-dimethoxyphenyl)-2,3-dihydropyridazin-3-on-2
6-(thien-2-yl)-2,3-dihydropyridazin-3-on-2
6-phenyl-4-methyl-2,3-dihydropyridazin-3-on-2
6-(4-methoxyphenyl)-4-methyl-2,3-dihydropyridazin-3-on-2
6-(4-chlorophenyl)-4-methyl-2,3-dihydropyridazin-3-on-2
6-(4-chlorophenyl )-5-methyl-2,3-dihydropyridazin-3-on-2
6-(4-carboxyphenyl)-4-methyl-2,3-dihydropyridazin-3-on-2
6-(2,5-dimethoxyphenyl) -4-methyl-2,3-dihydropyridazin-3-on-2
6-(3,4-dimethoxyphenyl)-4-methyl-2,3-dihydropyridazin-3-on-2
6-(thien-2-yl)-4-methyl-2,3-dihydropyridazin-3-on-2
6-methyl-2,3-dihydropyridazin-3-on-2, FAB 484
4,6-dimethyl-2,3-dihydropyridazin-3-on-2, FAB 498
4-propyl-6-methyl-2,3-dihydropyridazin-3-on-2
4-methyl-6-propyl-2,3-dihydropyridazin-3-on-2
5,6-dimethyl-2,3-dihydropyridazin-3-on-2
4,5,6-trimethyl-2,3-dihydropyridazin-3-on-2
4-methyl-2,3-dihydropyridazin-3-on-2
5-(4-methoxyphenyl)-2H-3,6-dihydro-1,3,4-thiadiazin-2-on-3
5-(3,4-dimethoxyphenyl)-6-ethyl-2H-3,6-dihydro-1,3,4-thiadiazin-2-on-3.

Analogously, by reaction of 4-methoxybenzenesulfonamide with the 2-(1,3-benzodioxol-5-yl)-2-(T-yl)acetic acids below,
in which T is
6-phenyl-2,3,4,5-tetrahydropyridazin-3-on-2
6-(4-methoxyphenyl)-2,3,4,5-tetrahydropyridazin-3-on-2
6-(4-chlorophenyl)-2,3,4,5-tetrahydropyridazin-3-on-2
6-(4-carboxyphenyl)-2,3,4,5-tetrahydropyridazin-3-on-2
6-carboxy-2,3,4,5-tetrahydropyridazine-3-one
6-(2,5-dimethoxyphenyl)-2,3,4,5-tetrahydropyridazin-3-on-2
6-(3,4-dimethoxyphenyl)-2,3,4,5-tetrahydropyridazin-3-on-2
6-(2,4-dimethoxyphenyl)-2,3,4,5-tetrahydropyridazin-3-one
6-(thien-2-yl)-2,3,4,5-tetrahydropyridazin-3-on-2
6-phenyl-4-methyl-2,3,4,5-tetrahydropyridazin-3-on-2
6-(4-methoxyphenyl)-4-methyl-2,3,4,5-tetrahydropyridazin-3-on-2

6-(4-chlorophenyl)-4-methyl-2,3,4,5,-tetrahydropyridazin-3-on-2
6-(4-carboxyphenyl)-4-methyl-2,3,4,5-tetrahydropyridazin-3-on-2
6-(2,5-dimethoxyphenyl)-4-methyl-2,3,4,5-tetrahydropyridazin-3-on-2
6-(3,4-dimethoxyphenyl)-4-methyl-2,3,4,5-tetrahydropyridazin-3-on-2
6-(thien-2-yl)-4-methyl-2,3,4,5-tetrahydropyridazin-3-on-2
6-methyl-2,3,4,5-tetrahydropyridazin-3-on-2
4,4,6-trimethyl-2,3,4,5-tetrahydropyridazin-3-on-2
4,6-dimethyl-2,3,4,5-tetrahydropyridazin-3-on-2
6-phenyl-2,3-dihydropyridazin-3-on-2
6-(4-methoxyphenyl)-2,3-dihydropyridazin-3-on-2
6-(4-chlorophenyl)-2,3-dihydropyridazin-3-on-2
6-(4-carboxyphenyl)-2,3-dihydropyridazin-3-on-2
6-(2,5-dimethoxyphenyl)-2,3-dihydropyridazin-3-on-2
6-(3,4-dimethoxyphenyl)-2,3-dihydropyridazin-3-on-2
6-(thien-2-yl)-2,3-dihydropyridazin-3-on-2
6-phenyl-4-methyl-2,3-dihydropyridazin-3-on-2
6-(4-methoxyphenyl)-4-methyl-2,3-dihydropyridazin-3-on-2
6-(4-chlorophenyl)-4-methyl-2,3-dihydropyridazin-3-on-2
6-(4-chlorophenyl)-5-methyl-2,3-dihydropyridazin-3-on-2
6-(4-carboxyphenyl)-4-methyl-2,3-dihydropyridazin-3-on-2
6-(2,5-dimethoxyphenyl)-4-methyl-2,3-dihydropyridazin-3-on-2
6-(3,4-dimethoxyphenyl)-4-methyl-2,3-dihydropyridazin-3-on-2
6-(thien-2-yl)-4-methyl-2,3-dihydropyridazin-3-on-2
6-methyl-2,3-dihydropyridazin-3-on-2, FAB 458
4,6-dimethyl-2,3-dihydropyridazin-3-on-2, EI 471
4-propyl-6-methyl-2,3-dihydropyridazin-3-on-2
4-methyl-6-propyl-2,3-dihydropyridazin-3-on-2
5,6-dimethyl-2,3-dihydropyridazin-3-on-2
4,5,6-trimethyl-2,3-dihydropyridazin-3-on-2
4-methyl-2,3-dihydropyridazin-3-on-2
5-(4-methoxyphenyl)-2H-3,6-dihydro-1,3,4-thiadiazin-2-on-3
5-(3,4-dimethoxyphenyl)-6-ethyl-2H-3,6-dihydro-1,3,4-thiadiazin-2-on-3.

the following 2-(1,3-benzodioxol-5-yl)-2-(T-yl)N-(4-methoxyphenylsulfonyl)acetamides are obtained,
in which T is
6-phenyl-2,3,4,5-tetrahydropyridazin-3-on-2
6-(4-methoxyphenyl)-2,3,4,5-tetrahydropyridazin-3-on-2
6-(4-chlorophenyl)-2,3,4,5-tetrahydropyridazin-3-on-2
6-(4-carboxyphenyl)-2,3,4,5-tetrahydropyridazin-3-on-2
6-carboxy-2,3,4,5-tetrahydropyridazine-3-one
6-(2,5-dimethoxyphenyl)-2,3,4,5-tetrahydropyridazin-3-on-2
6-(3,4-dimethoxyphenyl)-2,3,4,5-tetrahydropyridazin-3-on-2
6-(2,4-dimethoxyphenyl)-2,3,4,5-tetrahydropyridazin-3-one
6-(thien-2-yl)-2,3,4,5-tetrahydropyridazin-3-on-2
6-phenyl-4-methyl-2,3,4,5-tetrahydropyridazin-3-on-2
6-(4-methoxyphenyl)-4-methyl-2,3,4,5-tetrahydropyridazin-3-on-2
6-(4-chlorophenyl)-4-methyl-2,3,4,5,-tetrahydropyridazin-3-on-2
6-(4-carboxyphenyl)-4-methyl-2,3,4,5-tetrahydropyridazin-3-on-2
6-(2,5-dimethoxyphenyl)-4-methyl-2,3,4,5-tetrahydropyridazin-3-on-2
6-(3,4-dimethoxyphenyl)-4-methyl-2,3,4,5-tetrahydropyridazin-3-on-2
6-(thien-2-yl)-4-methyl-2,3,4,5-tetrahydropyridazin-3-on-2
6-methyl-2,3,4,5-tetrahydropyridazin-3-on-2
4,4,6-trimethyl-2,3,4,5-tetrahydropyridazin-3-on-2
4,6-dimethyl-2,3,4,5-tetrahydropyridazin-3-on-2
6-phenyl-2,3-dihydropyridazin-3-on-2
6-(4-methoxyphenyl)-2,3-dihydropyridazin-3-on-2
6-(4-chlorophenyl)-2,3-dihydropyridazin-3-on-2
6-(4-carboxyphenyl)-2,3-dihydropyridazin-3-on-2
6-(2,5-dimethoxyphenyl)-2,3-dihydropyridazin-3-on-2
6-(3,4-dimethoxyphenyl)-2,3-dihydropyridazin-3-on-2
6-(thien-2-yl)-2,3-dihydropyridazin-3-on-2
6-phenyl-4-methyl-2,3-dihydropyridazin-3-on-2
6-(4-methoxyphenyl)-4-methyl-2,3-dihydropyridazin-3-on-2
6-(4-chlorophenyl)-4-methyl-2,3-dihydropyridazin-3-on-2
6-(4-chlorophenyl)-5-methyl-2,3-dihydropyridazin-3-one
6-(4-carboxyphenyl)-4-methyl-2,3-dihydropyridazin-3-on-2
6-(2,5-dimethoxyphenyl)-4-methyl-2,3-dihydropyridazin-3-on-2
6-(3,4-dimethoxyphenyl)-4-methyl-2,3-dihydropyridazin-3-on-2
6-(thien-2-yl)-4-methyl-2,3-dihydropyridazin-3-on-2
6-methyl-2,3-dihydropyridazin-3-on-2, FAB 458
4,6-dimethyl-2,3-dihydropyridazin-3-on-2, EI 471
4-propyl-6-methyl-2,3-dihydropyridazin-3-on-2
4-methyl-6-propyl-2,3-dihydropyridazin-3-on-2
5,6-dimethyl-2,3-dihydropyridazin-3-on-2
4,5,6-trimethyl-2,3-dihydropyridazin-3-on-2
4-methyl-2,3-dihydropyridazin-3-on-2
5-(4-methoxyphenyl)-2H-3,6-dihydro-1,3,4-thiadiazin-2-on-3
5-(3,4-dimethoxyphenyl)-6-ethyl-2H-3,6-dihydro-1,3,4-thiadiazin-2-on-3.

EXAMPLE 4

Analogously to Example 1, by reaction of 4, 6-dimethyl-2,3-dihydropyridazin-3-one with the following methyl M-bromoacetates,
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl 2- difluoromethoxy phenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4- yl
2-methoxycarbonylmethoxy-4-methoxyphenyl
the following methyl 2-(M)-2- (4,6-dimethyl-2,3-dihydropyridazin-3-on-2-yl) acetates are obtained,
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-methoxycarbonylmethoxy-4-methoxyphenyl.

Analogously, by reaction of 6-(4-methoxyphenyl)-2,3,4,5-tetrahydropyridazin-3-one with the following methyl M-bromoacetates,
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-methoxycarbonylmethoxy-4-methoxyphenyl,
the following methyl 2-(M)-2-(6-(4-methoxyphenyl)-2, 3,4,5-tetrahydropyridazin-3-on-2-yl)acetates are obtained,
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-methoxycarbonylmethoxy-4-methoxyphenyl.

Analogously, by reaction of 6-(4-chlorophenyl)-2,3,4,5-tetrahydropyridazin-3-one with the following methyl M-bromoacetates,
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl 4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-methoxycarbonylmethoxy-4-methoxyphenyl,
the following methyl-2-(M)-2-(6-(4-chlorophenyl)-2, 3,4,5-tetrahydropyridazin-3-on-2-yl)acetates are obtained
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-methoxycarbonylmethoxy-4-methoxyphenyl.

Analogously, by reaction of 6- (3,4-dimethoxyphenyl)-2,3,4,5-tetrahydropyridazin-3-one with the following methyl M-bromoacetates,
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-methoxycarbonylmethoxy-4-methoxyphenyl,
the following methyl 2-(M)-2-(6-(3,4-dimethoxyphenyl)-2,3,4,5-tetrahydropyridazin-3-on-2-yl)acetates are obtained,
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-methoxycarbonylmethoxy-4-methoxyphenyl.

EXAMPLE 5

Analogously to Example 2, by hydrolysis of the following
methyl 2-(M)-2-(4,6-dimethyl-2,3-dihydropyridazin-3-on-2-yl)acetates,
methyl 2-(M)-2-(6-(4-methoxyphenyl)-2,3,4,5-tetrahydropyridazin-3-on-2-yl)acetates
methyl 2-(M)-2-(6-(4-chlorophenyl)-2,3,4,5-tetrahydropyridazin-3-on-2-yl)acetates and
methyl 2-(M)-2-(6-(3,4-dimethoxyphenyl)-2,3,4,5-tetrahydropyridazin-3-on-2-yl)acetates,
in which M is
phenyl 1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-methoxycarbonylmethoxy-4-methoxyphenyl,
the following
  2-(M)-2-(4,6-dimethyl-2,3-dihydropyridazin-3-on-2-yl)-acetic acids,
  in which M is
  phenyl
  1,4-benzodioxan-5-yl
  1,3-benzodioxol-4-yl
  2-methoxyphenyl
  3-methoxyphenyl
  4-methoxyphenyl, m.p. 204°
  2-methoxycarbonylphenyl
  3-methoxycarbonylphenyl
  4-methoxycarbonylphenyl
  2,3-dimethoxyphenyl
  2,4-dimethoxyphenyl
  2,3-dimethoxyphenyl
  3,4-dimethoxyphenyl
  3,5-dimethoxyphenyl
  4-cyanophenyl
  2,1,3-benzothiadiazol-5-yl
  2,1,3-benzooxadiazol-5-yl
  5-dimethylaminonaphthyl
  2-difluoromethoxyphenyl
  3-difluoromethoxyphenyl
  4-difluoromethoxyphenyl
  4-methyl-2,1,3-benzothiadiazol-5-yl
  4-trifluoromethyl-2,1,3-benzothiadiazol-5-yl
  7-bromo-2,1,3-benzothiadiazol-5-yl
  4-ethoxycarbonyl-2,1,3-benzothiadiazol-5-yl
  4-chloro-2,1,3-benzooxadiazol-5-yl
  6-nitro-2,1,3-benzooxadiazol-5-yl
  4-bromo-6-tert-butyl-2,1,3-benzooxadiazol-5-yl
  4-cyano-2,1,3-benzooxadiazol-5-yl
  2,1,3-benzothiadiazol-4-yl
  2-carboxymethoxy-4-methoxyphenyl,
  2-(M)-2-(-(4-methoxyphenyl)-2,3,4,5-tetrahydropyridazin-3-on-2-yl)acetic acids,
  in which M is
  phenyl
  1,4-benzodioxan-5-yl
  1,3-benzodioxol-4-yl
  2-methoxyphenyl
  3-methoxyphenyl
  4-methoxyphenyl
  2-methoxycarbonylphenyl
  3-methoxycarbonylphenyl
  4-methoxycarbonylphenyl
  2,3-dimethoxyphenyl
  2,4-dimethoxyphenyl
  2,5-dimethoxyphenyl
  3,4-dimethoxyphenyl
  3,5-dimethoxyphenyl
  4-cyanophenyl
  2,1,3-benzothiadiazol-5-yl
  2,1,3-benzooxadiazol-5-yl
  5-dimethylaminonaphthyl
  2-difluoromethoxyphenyl
  3-difluoromethoxyphenyl
  4-difluoromethoxyphenyl
  4-methyl-2,1,3-benzothiadiazol-5-yl
  4-trifluoromethyl-2,1,3-benzothiadiazol-5-yl
  7-bromo-2,1,3-benzothiadiazol-5-yl
  4-ethoxycarbonyl-2,1,3-benzothiadiazol-5-yl
  4-chloro-2,1,3-benzooxadiazol-5-yl
  6-nitro-2,1,3-benzooxadiazol-5-yl
  4-bromo-6-tert-butyl-2,1,3-benzooxadiazol-5-yl
  4-cyano-2,1,3-benzooxadiazol-5-yl
  2,1,3-benzothiadiazol-4-yl
  2-methoxycarbonylmethoxy-4-methoxyphenyl,
  2-(M)-2-(6-(4-chlorophenyl)-2,3,4,5-tetrahydropyridazin-3-on-2-yl)acetic acids,
  in which M is
  phenyl
  1,4-benzodioxan-5-yl
  1,3-benzodioxol-4-yl
  2-methoxyphenyl
  3-methoxyphenyl
  4-methoxyphenyl
  2-methoxycarbonylphenyl
  3-methoxycarbonylphenyl
  4-methoxycarbonylphenyl
  2,3-dimethoxyphenyl
  2,4-dimethoxyphenyl
  2,5-dimethoxyphenyl
  3,4-dimethoxyphenyl
  3,5-dimethoxyphenyl
  4-cyanophenyl
  2,1,3-benzothiadiazol-5-yl
  2,1,3-benzooxadiazol-5-yl
  5-dimethylaminonaphthyl
  2-difluoromethoxyphenyl
  3-difluoromethoxyphenyl
  4-difluoromethoxyphenyl
  4-methyl-2,1,3-benzothiadiazol-5-yl
  4-trifluoromethyl-2,1,3-benzothiadiazol-5-yl
  7-bromo-2,1,3-benzothiadiazol-5-yl
  4-ethoxycarbonyl-2,1,3-benzothiadiazol-5-yl
  4-chloro-2,1,3-benzooxadiazol-5-yl
  6-nitro-2,1,3-benzooxadiazol-5-yl
  4-bromo-6-tert-butyl-2,1,3-benzooxadiazol-5-yl
  4-cyano-2,1,3-benzooxadiazol-5-yl
  2,1,3-benzothiadiazol-4-yl
  2-carboxymethoxy-4-methoxyphenyl,
  and 2-(M)-2- (6-(3,4-dimethoxyphenyl) -2,3,4,5-
tetrahydropyridazin-3-on-2-yl) acetic acids,
in which M is
phenyl
1,4-benzodioxan- 5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-carboxymethoxy-4-methoxyphenyl, are obtained.

EXAMPLE 6

Analogously to Example 3, by reaction of 4-isopropylbenzenesulfonamide with the
2-(M)-2-(4,6-dimethyl-2,3-dihydropyridazin-3-on-2-yl)-acetic acids,
2-(M)-2-(6-(4-methoxyphenyl)-2,3,4,5-tetrahydropyridazin-3-on-2-yl)acetic acids,
2-(M)-2-(6-(4-chlorophenyl)-2,3,4,5-tetrahydropyridazin-3-on-2-yl)acetic acids, and
2-(M)-2-(6-(3,4-dimethoxyphenyl)-2,3,4,5-tetrahydropyridazin-3-on-2-yl)acetic acids below,
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxy phenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol -5-yl
4-trifluoromethyl-2,1,3-benzothiadiazol -5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3- benzothiadiazol-4-yl
2-carboxymethoxy-4-methoxyphenyl,
the following
2-(M)-2-(4,6-dimethyl-2,3-dihydropyridazin-3-on-2-yl)-N-(4-isopropylphenylsulfonyl)acetamides,
in which M is
phenyl
1,4-benzodioxan-5-yl
1,3-benzodioxol-4-yl
2-methoxyphenyl
3-methoxyphenyl
4-methoxyphenyl, m.p. 275° (decomposition)
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-carboxymethoxy-4-methoxyphenyl,
2-(M)-2-(6-(4-methoxyphenyl)-2,3,4,5-tetrahydropyridazin-3-on-2-yl)N-(4-isopropylphenylsulfonyl)-acetamides,
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl 2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-carboxymethoxy-4-methoxyphenyl, 2-(M)-2-(6-(4-chlorophenyl)-2,3,4,5-tetrahydropyridazin-3-on-2-yl)N-(4-isopropylphenylsulfonyl)-acetamides,
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-carboxymethoxy-4-methoxyphenyl,
and 2-(M)-2-(6-(3,4-dimethoxyphenyl)-2,3,4,5-tetrahydropyridazin-3-on-2-yl)N-(4-isopropylphenylsulfonyl)-acetamides,
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-carboxymethoxy-4-methoxyphenyl,
are obtained.

Analogously, by reaction of 4-tert-butylbenzenesulfonamide with the abovementioned acetic acid derivatives the 2-(M)-2-(4,6-dimethyl-2,3-dihydropyridazin-3-on-2-yl)-N-(4-tert-butylphenylsulfonyl)acetamides below,
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-carboxymethoxy-4-methoxyphenyl 2-(M)-2-(6-(4-methoxyphenyl)-2,3,4,5-tetrahydropyridazin-3-on-2-yl)N-(4-tert-butylphenylsulfonyl)-acetamides,
in which M is
phenyl
1,4-benzodioxan-5-yl
1,3-benzodioxol-4-yl
2-methoxyphenyl
3-methoxyphenyl 4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-carboxymethoxy-4-methoxyphenyl 2-(M)-2-(6-(4-chlorophenyl)-2,3,4, 5-tetrahydropyridazin-3-on-2-yl)N-(4-tert-butylphenylsulfonyl)-acetamides,
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonylphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-carboxymethoxy-4-methoxyphenyl
and 2-(M)-2-(6-(3,4-dimethoxyphenyl)-2,3,4, 5-tetrahydropyridazin-3-on-2-yl)N-(4-tert-butylphenylsulfonyl)-acetamides,
in which M is
phenyl
1,4-benzodioxan-5-yl
1,3-benzodioxol-4-yl
2-methoxyphenyl
3-methoxyphenyl
4-methoxyphenyl
2-methoxycarbonylphenyl
3-methoxycarbonyphenyl
4-methoxycarbonylphenyl
2,3-dimethoxyphenyl
2,4-dimethoxyphenyl
2,5-dimethoxyphenyl
3,4-dimethoxyphenyl
3,5-dimethoxyphenyl
4-cyanophenyl
2,1,3-benzothiadiazol-5-yl
2,1,3-benzooxadiazol-5-yl
5-dimethylaminonaphthyl
2-difluoromethoxyphenyl
3-difluoromethoxyphenyl
4-difluoromethoxyphenyl
4-methyl-2,1,3-benzothiadiazol-5-yl
4-trifluoromethyl-2,1,3-benzothiadiazol-5-yl
7-bromo-2,1,3-benzothiadiazol-5-yl
4-ethoxycarbonyl-2,1,3-benzothiadiazol-5-yl
4-chloro-2,1,3-benzooxadiazol-5-yl
6-nitro-2,1,3-benzooxadiazol-5-yl
4-bromo-6-tert-butyl-2,1,3-benzooxadiazol-5-yl
4-cyano-2,1,3-benzooxadiazol-5-yl
2,1,3-benzothiadiazol-4-yl
2-carboxymethoxy-4-methoxyphenyl,
are obtained.

EXAMPLE 7

Analogously to Example 3, by reaction of (5-dimethylaminonaphthyl)-sulfonamide with 2-(1,3-benzodioxol-5-yl)-2-(6-methyl-2,3-dihydropyridazin-3-on-2-yl)acetic acid ("A") the compound 2-(1, 3-benzodioxol-5-yl)-2-(6-methyl-2,3-dihydropyridazin-3-on-2-yl)-N-(5-dimethylaminonaphthyl-sulfonyl)acetamide is obtained, FAB 521.

Analogously, by reaction of "A"
with benzenesulfonamide
2-(1,3-benzodioxol-5-yl)-2-(6-methyl-2, 3-dihydropyridazin-3-on-2-yl)-N-(phenylsulfonyl) acetamide, EI 427, is obtained, and
with 4-bromo-benzenesulfonamide
2-(1,3-benzodioxol-5-yl)-2-(6-methyl-2,3-dihydropyridazin-3-on-2-yl)-N-(4-bromophenylsulfonyl)-acetamide, FAB 506, is obtained,
and with biphenylsulfonamide
2-(1,3-benzodioxol-5-yl)-2-(6-methyl-2,3-dihydropyridazin-3-on-2-yl)-N-(biphenylsulfonyl) acetamide, FAB 504, is obtained.

EXAMPLE 8

Analogously to Example 1 and 2, by reaction of methyl benzo[1,3]dioxol-5-ylbromoacetate ("B") with 6-(pyridine-2-yl)-2,3-dihydropyridazin-3-one and subsequent hydrolysis the compound
2-(1,3-benzodioxol-5-yl)-2-(6-(pyridine-2-yl)-2,3-dihydropyridazin-3-on-2-yl)acetic acid, m.p. 115°, is obtained,
and by reaction of methyl(4-methoxyphenyl)-bromoacetate with 4-(4-methoxybenzyl)-6-methyl-2,3-dihydropyridazin-3-one and subsequent hydrolysis the compound 2-(4-methoxyphenyl)-2-(4-(4-methoxybenzyl)-6-methyl-2,3-dihydro-pyridazin-3-on-2-yl)acetic acid, EI 408, is obtained, and by reaction of "B" with 4-(4-methoxybenzyl)-6-(4-methoxyphenyl)-2,3-dihydropyridazin-3-one and subsequent hydrolysis the compound 2-(1,3-benzodioxol-5-yl)-2-(4-(4-methoxybenzyl)-6-(4-methoxyphenyl)-2,3-dihydropyridazin-3-on-2-yl) acetic acid is obtained.

Analogously, 2-(1,3-benzodioxol-5-yl)-2-(4-(2-methoxybenzyl)-6-(4-methoxyphenyl)-2,3-dihydropyridazin-3-on-2-yl)acetic acid, FAB 501, is obtained, and by reaction of "B" with 6-trifluoromethyl-2,3-dihydropyridazin-3-one and subsequent hydrolysis the compound 2-(1,3-benzodioxol-5-yl)-2-(6-trifluoromethyl-2,3-dihydropyridazin-3-on-2-yl)acetic acid, FAB 343, is obtained.

Analogously, by reaction of "B" with 4-phenyl-6-cyclopropyl-2,3-dihydro-pyridazin-3-on and subsequent hydrolysis the compound 2-(1,3-benzodioxol-5-yl)-2-(4-phenyl-6-cyclopropyl-2,3-dihydropyridazin-3-on-2-yl)acetic acid, m.p. 176°, is obtained.

The following examples relate to pharmaceutical preparations:

Example A: Injection vials

A solution of 100 g of an active compound of the formula I and 5 g of disodium hydrogen phosphate are adjusted to pH 6.5 in 3 l of double-distilled water using 2N hydrochloric acid, sterile-filtered, filled into injection vials, lyophilized under sterile conditions and asceptically sealed. Each injection vial contains 5 mg of active compound.

Example B: Suppositories

A mixture of 20 g of an active compound of the formula I is fused with 100 g of soya lecithin and 1400 g of cocoa butter, poured into molds and allowed to cool. Each suppository contains 20 mg of active compound.

Example C: Solution

A solution of 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water is prepared. The mixture is adjusted to pH 6.8, made up to 1 l and sterilized by irradiation. This solution can be used in the form of eye drops.

Example D: Ointment 500 mg of an active compound of the formula I is mixed with 99.5 g of petroleum jelly under aseptic conditions.

Example E: Tablets

A mixture of 1 kg of active compound of the formula I, 4 kg of lactose, 1.2 kg of potato starch, 0.2 kg of talc and 0.1 kg of magnesium stearate is compressed to give tablets in the customary manner such that each tablet contains 10 mg of active compound.

Example F: Coated tablets

Analogously to Example E, tablets are pressed which are then coated in a customary manner with a coating of sucrose, potato starch, talc, tragacanth and colorants.

Example G: Capsules 2 kg of active compound of the formula I are formed into hard gelatine capsules in a customary manner such that each capsule contains 20 mg of the active compound.

Example H: Ampoules

A solution of 1 kg of active compound of the formula I in 60 l of double-distilled water is sterile-filtered, filled into ampoules, lyophilized under sterile conditions and aseptically sealed. Each ampoule contains 10 mg of active compound.

We claim:

1. A compound of formula I

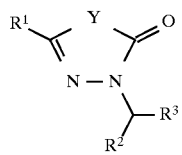

wherein
Y is $-C(R^4R^{4'})C(R^4R^{4'})$, $-CR^4=CR^{4'}-$ or $C(R^4R^4)S-$,
$R^1$ is Het, Ar, $R^3$ or $R^4$,
$R^2$ is Ar or a

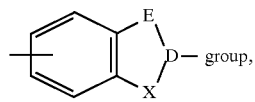 group, which is unsubstituted or mono- or disubstituted in the phenyl moiety by A, $R^3$, $OR^4$, $NH_2$, NHA, $NA_2$, $NO_2$, CN, Hal, $NHCOR^4$, $NHSO_2R^4$, $COOR^4$, $COR^4$, $CONHSO_2R^6$, $O(CH_2)_nR^3$, OPh, $O(CH_2)_nOR^4$ or $S(O)_mR^4$ or a

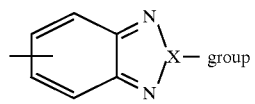 group which is unsubstituted or mono- or disubstituted in the cyclohexyldienyl moiety by A, $R^3$, $OR^4$, $NH_2$, NHA, $NA_2$, $NO_2$, CN, Hal, $NHCOR^4$, $NHSO_2R^4$, $COOR^4$, $COR^4$, $CONHSO_2R^6$, $O(CH_2)_nR^3$, OPh, $O(CH_2)_nOR^4$ or $S(O)_mR^4$, $R^3$ is CN, COOH, COOA, $CONHSO_2R^5$ or 1H-tetrazol-5-yl $R^4, R^{4'}$ in each case independently of one another are H, A or phenyl or benzyl which is unsubstituted or monosubstituted by alkoxy, $R^5$ is A or Ar, $R^6$ is phenyl or naphthyl which is unsubstituted or mono-, di- or trisubstituted by A, $OR^5$, $NH_2$, NHA, $NA_2$, $NO_2$ CN or Hal, A is alkyl having 1–6 C atoms, in which one or two $CH_2$ groups can be replaced by O or S atoms or by $-CR^4=CR^{4'}$ groups and also 1–7 H atoms can be replaced by F or is benzyl, Ar is phenyl or naphthyl, which is unsubstituted or mono-, di- or trisubstituted by A, $OR^4$, $NH_2$, NHA, $NA_2$, $NO_2$, CN, Hal, $NHCOR^4$, $NHSO_2R^4$, $COOR^4$, $COR^4$, $CONHSO_2R^6$, $O(CH_2)_nR^3$, OPh, $O(CH_2)_nOR^4$ or $S(O)_mR^4$, Het is a mono- or bicyclic saturated, unsaturated or aromatic heterocycle having 1 to 4 N, O and/or S atoms, bonded via N or C, which can be unsubstituted or mono-, di- or trisubstituted by Hal, A, $R^3$, $NH_2$, NHA, $NA_2$, CN, $NO_2$ and/or carbonyl oxygen, D is carbonyl or $_n$, E is $CH_2$, S or O, Hal is F, Cl, Br or I, X is 0 or S, m is 0, 1 or 2, n is 1 or 2, or a salt thereof, with the proviso that $R^2$ is not unsubstituted phenyl.

2. a) 2-(1,3-Benzodioxol-5-yl)-2-(2,3-dihydro-4,6-dimethylpyridazin-3-on-2-yl)N-(4-isopropylphenylsulfonyl)acetamide;

b) 2-(1,3-benzodioxol-5-yl)-2-(6-(4-methoxyphenyl)-2,3,4,5-tetrahydropyridazin-3-on-2-yl)N-(4-isopropylphenylsulfonyl)-acetamide;

c) 2-(1,3-benzodioxol-5-yl)-2-(6-(4-chlorophenyl)-2,3,4,5-tetrahydropyridazin-3-on-2-yl)N-(4-isopropylphenylsulfonyl)acetamide;

d) 2-(1,3-benzodioxol-5-yl)-2-(6-(3,4-dimethoxyphenyl)-2,3,4,5-tetrahydropyridazin-3-on-2-yl)N-(4-isopropylphenylsulfonyl)-acetamide;

e) 2-(1,3-benzodioxol-5-yl)-2-(4-methyl-6-phenyl-2,3-dihydropyridazin-3-on-2-yl)N-(4-isopropylphenylsulfonyl) acetamide; or f) 2-(1,3-benzodioxol-5-yl)-2-(5-(3,4-dimethoxyphenyl)-6-ethyl-2H-3,6-dihydro-1,3,4-thiadiazin-2-on-3-yl)N-(4-isopropylphenylsulfonyl) acetamide, each a compound of claim 1.

3. A process for preparing a compound of formula I according to claim 1 and a salt thereof, comprising reacting a compound of formula II

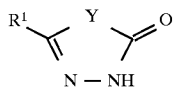
II wherein $R^1$ and Y have the meanings indicated in claim 1, with a compound of formula III

III wherein

Q is Cl, Br, I or a free or reactive functionally modified OH group and $R^2$ and $R^3$ have the meanings indicated in claim 1, and/or converting one or more radicals $R^1$, $R^2$ and/or $R^3$ in a compound of formula I into one or more radicals $R^1$, $R^2$ and/or $R^3$ by, i) hydrolysing an ester group to a carboxyl group, ii) converting a carboxyl group into a sulfonamidocarbonyl group and/or converting a base or acid of a compound of formula I into one of its salts.

4. A pharmaceutical preparation, comprising an effective amount of at least one compound of formula I of claim 1 and/or one of its physiologically acceptable salts, and a pharmaceutically acceptable excipient.

5. A method of treating hypertension, cardiac insufficiency, renal insufficiency, cerebral infarct, coronary heart disease, renal, cerebral and myocardial ischaemia, subarachnoid haemorrhage, inflammations, asthma, endotoxic shock in a patient in need of such treatment, comprising administering an effective amount of a compound of claim 1 or a physiologically acceptable salt thereof.

* * * * *